United States Patent [19]

Schwab, Jr.

[11] Patent Number: 5,086,291
[45] Date of Patent: Feb. 4, 1992

[54] SENSING MAT, AND METHODS OF CONSTRUCTING AND UTILIZING SAME

[76] Inventor: Henry J. Schwab, Jr., 429 Rittenhouse Cir., Havertown, Pa. 19083

[21] Appl. No.: 430,146

[22] Filed: Nov. 1, 1989

[51] Int. Cl.⁵ .............................................. G08B 21/00
[52] U.S. Cl. ...................................... 340/604; 324/693
[58] Field of Search ............... 340/604, 605, 573, 562; 128/886; 604/361; 200/61.05; 324/65 R, 61 R, 664, 689, 693–694

[56] References Cited

U.S. PATENT DOCUMENTS

| | | |
|---|---|---|
| 2,127,538 | 8/1938 | Seiger . |
| 3,986,110 | 10/1976 | Verall et al. . |
| 4,083,038 | 4/1978 | Klebanoff . |
| 4,163,449 | 8/1979 | Regal ................... 128/886 |
| 4,191,950 | 3/1980 | Levin et al. ............ 340/604 |
| 4,212,295 | 7/1980 | Snyder ................... 128/886 |
| 4,297,686 | 10/1981 | Tom ...................... 340/604 |
| 4,319,232 | 3/1982 | Westphal et al. ........ 340/604 |
| 4,356,818 | 11/1982 | Macias et al. .......... 128/886 |
| 4,688,027 | 8/1987 | Widener ................. 340/604 |

Primary Examiner—Glen R. Swann, III.
Assistant Examiner—Thomas J. Mullen, Jr.
Attorney, Agent, or Firm—Irving M. Weiner; Robert M. Petrik; Joseph P. Carrier

[57] ABSTRACT

A device for sensing the presence of liquids or other substances and warning of potential hazards. The device includes a mat which is constructed of metallized sheets. This mat may be cut to any size or shape on site. A monitor device is electrically connected to the mat and monitors a change in capacitance or resistance of the mat. Such a change is an indication of the presence of unwanted substace. The monitoring device may then either activate an alarm or turn off any electrical device as deemed necessary.

10 Claims, 1 Drawing Sheet

SENSING MAT, AND METHODS OF CONSTRUCTING AND UTILIZING SAME

BACKGROUND OF THE INVENTION

1. Filed of the Invention

The present invention relates to warning or alarm systems and, more particularly, to an electrical device of variable size for use in signalling the presence of unwanted substances near sensitive equipment.

2. Description of the Relevant Art

Heretofore, there have been various means for signalling the presence of liquids.

U.S. Pat. No. 2,127,538 discloses a device for use in determining the presence of moisture in a child's bed. A series of wires are provided on a mat. When moisture contacts two wires, a relay switch is closed and an alarm, either audible or visual, will be activated.

This device cannot be varied in size since cutting of the device can result in the cutting of wires and shorting of the device.

U.S. Pat. No. 3,986,110 discloses a device for determining the depth of a liquid accumulating on its surface. The device is constructed of a non-conductive material with a web of elongated strips of foil. The device operates such that the presence of liquid affects the capacitance and conductance of the sensor.

Again, this device cannot be adapted to situations other than that discussed above.

U.S. Pat. No. 4,083,038 discloses a sensor for determining the level of a liquid in a container. The device employs a web of non-conductive material with electrically conducting plates spaced therein. As the liquid level in the container drops, the capacitance of the device changes to cause an alarm to be given.

The present invention provides a device capable of being sized and shaped for the given situation on site. In addition, the device is lightweight and easily transportable.

SUMMARY OF THE INVENTION

The present invention provides a readily adaptable, sensitive alarm or warning system. The system comprises a mat made of sheets including a conductive and non-conductive side and an electronic circuit monitor to check the resistance or the capacitance of the mat.

In a preferred embodiment, the mat comprises two sheets of "metalized" material. An example of this material is MYLAR sheets. Each sheet of this material must include a conductive side and non-conductive side. One sheet will include a pattern of apertures therethrough. The two sheets will be laminated together to form the mat. This mat may then be cut to any size or shape.

The circuit monitor may be attached to this mat by electrical leads. When unwanted material, either liquid, powder or metal shavings, contacts the mat in sufficient quantity to cause a change in resistance or capacitance of the mat, an alarm and/or switch is activated.

It is an object of the present invention to provide an alarm system which is readily adaptable to any situation.

It is a further object of the present invention to provide a lightweight, easily transportable device.

It is still a further object of the present invention to provide a mat which is flexible and can be cut to any size.

The above and further objects, details and advantages of the invention of the invention will become apparent from the following detailed description, when read in conjunction with the accompanying drawings.

DETAILED DESCRIPTION OF THE PREFERRED EMBODIMENT

Figure 1:
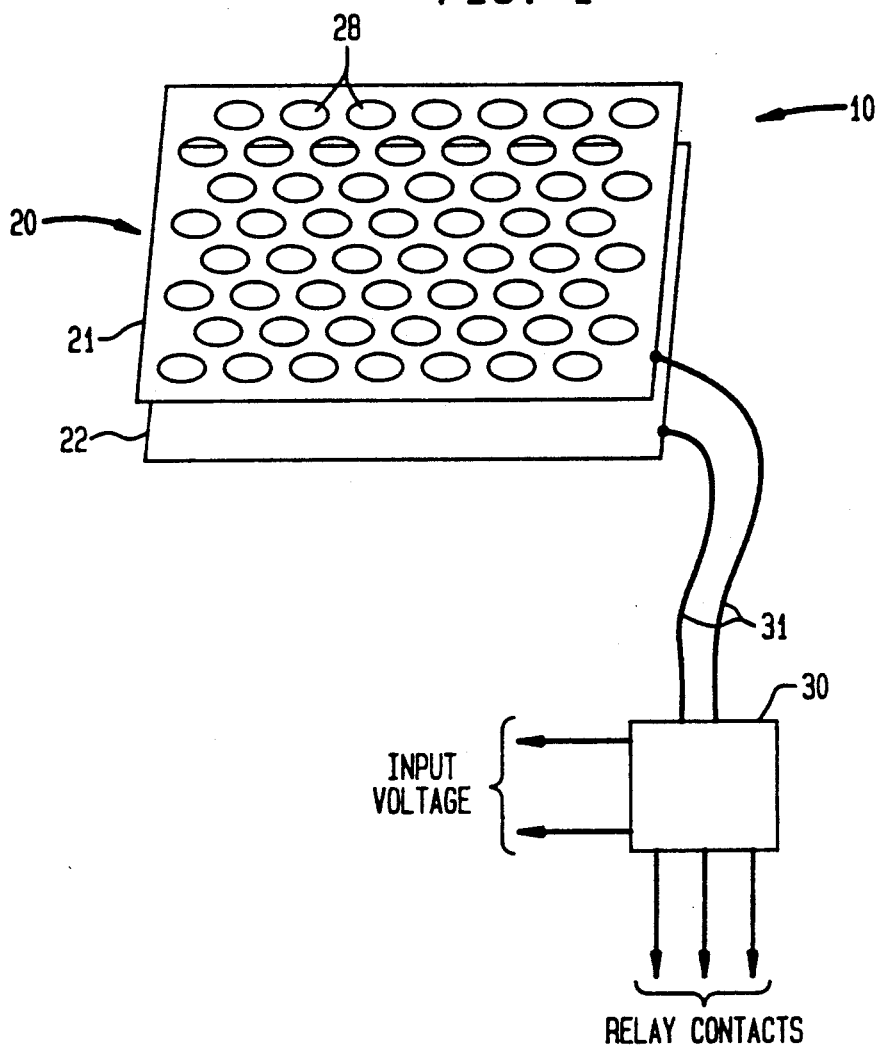
FIG. 1 illustrates an alarm/switch system in accordance with the present invention.

As shown in FIG. 1, the alarm/switch system 10 includes a thin, flexible mat 20 and monitoring circuit 30. The mat 20 is electrically connected to the monitoring means or circuit 30 by means such as leads 31. The leads 31 may be electrically connected to the mat by any known means including soldering. The leads 31 must be connected to the conductive sides of each sheet layer 21, 22.

Figure 2:
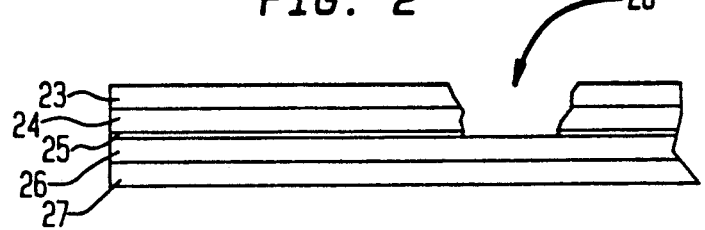
FIG. 2 illustrates a partial cross-section of a mat in accordance with the present invention.

Upper sheet 21 includes a pattern of apertures 28 therein. As best seen in FIG. 2, sheet 21 includes a conductive side 23 and non-conductive side 24. Conductive side 23 can include any type of well-known conductive material. Non-conductive side 24 may be paper, plastic or any other well-known insulative material. Side 24 must always be adjacent conductive side 26 of sheet 22. Preferably, the sheets 21, 22 are MYLAR.

Lower sheet 22 includes a conductive side 26 and preferably a non-conductive side 27.

Sheets 21, 22 are joined together by adhesive 25. Adhesive 25 does not entirely cover lower sheet 22 since the aperture 28 must permit unwanted substances to reach conductive layer 26.

Apertures 28 may comprise any pattern of holes, slots or slits or any combination thereof.

Monitoring means 30 is connected to a power source or voltage input and relay contacts which may turn off the electrical equipment or activate an alarm.

In use, a large sheet of mat 20 may be brought to the required location. Generally, the mat will be located where electrical or other sensitive equipment may be harmed by water or other unwanted substances.

Mat 20 may be cut to the desired size and shape. This flexibility permits the mat to be retrofitted to locations normally inaccessible to known sensors. The mat 20 may be placed in conjuction with a screen or grill to insulate it from vibrational damage which may be caused by an electric motor.

Once the leads 31 are attached to the mat 20, the monitor 30 will observe either the capacitance or the resistance of the mat. When a liquid or other material contacts the mat 20 and can contact both sheets 21, 22, or, in other words, conductive sides 26, 23, a shorted capacitance or lower resistance will result.

Upon sensing one of the changes set forth above, the monitoring circuit 30 may set off an alarm or turn the equipment off to prevent any damage.

The invention is characterized by simplicity, economy of manufacture, durability and convenience of use. Its compactness and ready adaptability to any situation renders the invention practical where the prior art has proved to be impractical.

Although there has been described what is at present considered to be preferred embodiments of the invention, it will be understood that various modifications and variations may be made therein, and it is intended to cover, in the appended claims, all such modifications as fall within the true spirit and scope of the invention.

I claim:

1. A warning device for the prevention of damage to electrical equipment by liquids, comprising:
    a thin, flexible mat which is adaptable to various situations by changing the size to meet the required conditions on site including conductive and nonconductive portions;
    a monitoring means for sensing changes in the electrical properties of said mat;
    means to electrically connect said mat to said monitoring means;
    upon sensing a change in the electrical properties of said mat, a warning device is activated by said monitoring means;
    said monitoring means deactivates said electrical equipment; and
    said mat may be cut to change the size and shape.

2. A warning device for the prevention of damage to property such as electrical equipment, comprising:
    a thin, flexible mat including conductive and nonconductive portions;
    said mat comprises two layers of metalized sheets;
    each said layer includes a conductive side and a nonconductive side;
    said two layers includes an upper layer and lower layer, said upper layer includes a pattern of apertures therein;
    said upper layer conductive side is facing upward;
    said lower layer conductive side is facing up and is adjacent said upper nonconductive side;
    a monitoring means for sensing changes in the electrical properties of said mat;
    means to electrically connect said mat to said monitoring means; and
    upon sensing a change in the electrical properties of said mat, a warning device is activated by said monitoring means.

3. The device of claim 2, wherein:
    said upper layer conductive side and said lower layer conductive side are electrically connected to said monitoring means by said means to electrically connect.

4. The device of claim 3, wherein:
    said upper layer and lower layer are laminated to form an integral mat.

5. The device of claim 3, wherein:
    said monitoring means senses a change in capacitance of said mat.

6. The device of claim 5, wherein:
    a change of capacitance of said mat results from an unwanted substance contacting both said upper and lower conductive sides via said apertures.

7. The device of claim 6, wherein:
    said change in capacitance results in a warning device being activated.

8. The device of claim 3, wherein:
    said monitoring means senses a change in resistance of said mat.

9. The device of claim 8, wherein:
    a change of resistance of said mat results from an unwanted substance contacting both said upper and lower conductive sides via said apertures.

10. The device of claim 9, wherein:
    said change in resistance results in a warning device being activated.

* * * * *

UNITED STATES PATENT AND TRADEMARK OFFICE
CERTIFICATE OF CORRECTION

PATENT NO. : 5,086,291

DATED : FEBRUARY 4, 1992

INVENTOR(S) : HENRY J. SCHWAB, JR.

It is certified that error appears in the above-identified patent and that said Letters Patent is hereby corrected as shown below:

In the Abstract, line 8, change "substace" to --substance--.

Column 1, line 6, change "Filed" to --Field--.

Signed and Sealed this

First Day of June, 1993

Attest:

MICHAEL K. KIRK

Attesting Officer

Acting Commissioner of Patents and Trademarks